United States Patent [19]

Radlmann et al.

[11] 4,018,809

[45] Apr. 19, 1977

[54] SOLUTIONS OF NEW ANTIMONY COMPLEXES

[75] Inventors: Eduard Radlmann; Heinz Schaffner; Günter Lorenz; Günther Nischk, all of Dormagen, Germany

[73] Assignee: Plumley and Tyner, Leverkusen, Germany

[22] Filed: Sept. 12, 1975

[21] Appl. No.: 612,712

[30] Foreign Application Priority Data

Sept. 12, 1974 Germany ........................ 2443572

[52] U.S. Cl. .............................. 260/446; 252/8.1; 260/45.75 B
[51] Int. Cl.[2] ........................................... C07F 9/90
[58] Field of Search ............... 260/446, 45.75 B; 252/8.1

[56] References Cited

UNITED STATES PATENTS

| | | | |
|---|---|---|---|
| 3,245,958 | 4/1966 | Hindersinn et al. | 252/8.1 |
| 3,657,179 | 4/1972 | Yates | 260/446 |
| 3,728,367 | 4/1973 | Yates | 260/446 |
| 3,763,202 | 10/1973 | Cumbo et al. | 260/45.75 B |

OTHER PUBLICATIONS

Chemical Abstracts, 57,5550g (1962).

*Primary Examiner*—Helen M. S. Sneed

[57] ABSTRACT

The invention relates to a process for the production of solutions of substantially water-insoluble complex antimony compounds in polar organic solvents by esterifying an α-hydroxy polycarboxylic acid with a polyol, reacting an excess of the esterification product with an antimony oxide in a polar organic solvent and reacting the free carboxylic groups with a monoisocyanate.

8 Claims, No Drawings

SOLUTIONS OF NEW ANTIMONY COMPLEXES

This invention relates to solutions of antimony compounds which are substantially insoluble in water and readily soluble in organic solvents. These solutions may be mixed with solutions of copolymers of acrylonitrile and vinyl or vinylidene halides without any signs of incompatibility, and as synergists reduce the inflammability of shaped articles obtained from mixtures of this kind to a very considerable extent.

It is known frum U.S. Pat No. 3,728,367 and DOS No. 2,159,174 that antimony (III)- and antimony (V)- α-hydroxy carboxylic acid complexes in polar organic solvents can be prepared from the corresponding antimony halides by splitting off the halogen through precipitation of ammonium halide and adding an α-hydroxy carboxylic acid, for example tartaric acid. It is possible in this way to produce complexes which are either completely free from halogen or which still contain halogen, depending upon the quantity of ammonia used. These complexes are miscible and compatible with solutions of copolymers of acrylonitrile and vinyl or vinylidene halides. However, the halogen-free types have the serious disadvantage of being soluble in water in any quantitative ratio. Moreover, the halogen-containing types have the disadvantage of hydrolysing on the addition of water, giving off hydrogen halide which causes corrosion in the apparatus used. After the polymer solutions have been processed into shaped articles, for example filaments, large quantities of the antimony are washed out during the usual aqueous aftertreatments as a result of the solubility in water of compounds of this kind, and hence become ineffective.

It is an object of this invention to provide a method for producing antimony complexes which do not exhibit these disadvantages.

Other objects will be evident from the description and the Examples.

These objects are accomplished by a process for the production of a solution of a substantially water-insoluble complex antimony compounds in a polar organic solvent which comprises esterifying an α-hydroxy polycarboxylic acid with a polyol in a molar ratio of the carboxyl groups to the hydroxyl groups in the polyol of at least 2 : 1 and in the presence of an acid transesterification catalyst; reacting an excess of the esterification product with an antimony oxide in a polar organic solvent at a temperature in the range of from 100° to 200° C to form a clear solution still containing free carboxyl groups; and adding a monoisocyanate to the solution at a temperature below 100° C in such a quantity that the free carboxyl groups are converted into the corresponding amide groups.

The polyols used are preferably compounds corresponding to the general formula:

$$R(OH)_n$$

in which R is a straight-chain or branched aliphatic radical having from 2 to 20 carbon atoms and $n$ is a number from 2 to 6. Examples of compounds of this kind are ethylene glycol, 1,4-butane diol, 1,6-hexane diol, glycerol, pentaerythritol and mannitol.

Suitable α-hydroxy carboxylic acids are, for example, tartaric acid, malic acid, citric acid and mucic acid. Tartaric acid and citric acid are preferably used.

The antimony oxides are $Sb_2O_3$ and $Sb_2O_5$, preferably $Sb_2O_3$.

The monoisocyanates used are preferably compounds corresponding to the general formula:

$$R_1-N=C=O$$

in which $R_1$ is a straight-chain or branched alkyl radical having from 1 to 20 carbon atoms, or represents the radical:

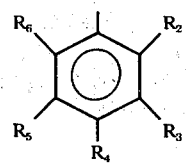

in which $R_2$, $R_3$, $R_4$, $R_5$ and $R_6$ may be the same as or different from one another and may represent hydrogen, an alkyl radical having from 1 to 5 carbon atoms, fluorine, chlorine or bromine.

Suitable polar organic solvents are, for example, formamide, monomethyl formamide, dimethyl formamide, acetamide, monomethyl acetamide, dimethyl acetamide, tetramethyl urea, N-methyl pyrrolidone and dimethyl sulphoxide. It is particularly preferred to use dimethyl formamide or dimethyl acetamide.

The following procedure for example may be adopted for preparing the new solutions by the process according to the invention: the α-hydroxy polycarboxylic acid, for example tartaric acid, is condensed in known manner with a polyol, for example ethylene glycol, the molar ratio of the carboxyl groups to the hydroxyl groups in the ethylene glycol being 2 : 1, in the presence of an acid transesterification catalyst, for example an acid ion exchanger, at temperatures in the range of from 100° to 200° C and preferably at temperatures in the range of from 100° to 180° C, an inert gas, for examle nitrogen, being passed over during the condensation reaction. The resulting precondensate is then dissolved in a polar solvent and heated with antimony (III) or antimony (V) oxide in a molar ratio of from 2 : 1 to 4 : 1 (ratio of free carboxyl groups to antimony) at temperatures in the range of from 100° to 200° C and preferably at temperatures in the range of from 100° to 180° C, while nitrogen is passed over until a solution is formed, water being eliminated in the meanwhile. The solution is then cooled to temperatures of below 100° C and diluted with more solvent according to the particular application envisaged, followed by addition of the stoichiometric quantity (based on the free carboxyl groups) of a monoisocyanate, preferably at 40° to 60° C. Carbonamide groups are formed with the evolution of carbon dioxide. The solutions obtained are substantially colourless and may readily be used as flameproofing additives. However, if the solvent is removed by distillation, a pale yellowish, solid residue is obtained. The major advantage of this new process for producing the new solutions of antimony compounds according to the invention is that it is possible to use antimony oxides, generally antimony trioxide, as the starting antimony compounds. The complications involved in using antimony halides and separating off the halogen by precipitation with ammonia are thereby eliminated. Accordingly, it is possible by virtue of the process according to the invention to obtain non-hydrolysing, i.e. non-corrosive, additives which are insoluble in water and which are not washed out of the end products during the usual aqueous aftertreatments.

Since, according to the invention, the α-hydroxy polycarboxylic acid and the polyol are used in a molar ratio of at least 2 : 1 (carboxyl groups : hydroxyl groups) and since on the other hand the molar ratio between the precondensate and the antimony oxide is generally in the range from 2 : 1 to 4 : 1, reaction mixtures rather than individual compounds are formed in the solution. The results of analytical investigations show that the following structures are probably the main components of the tartaric acid/ethylene glycol-/antimony trioxide/phenyl isocyanate system:

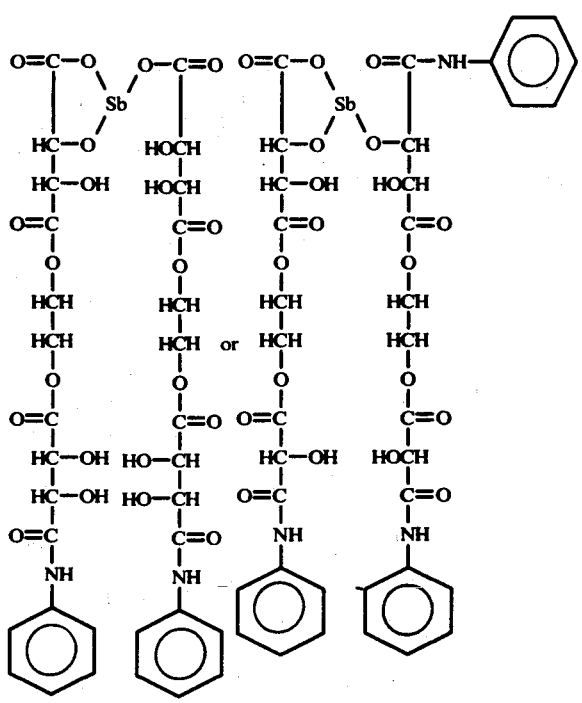

whereas compounds such as

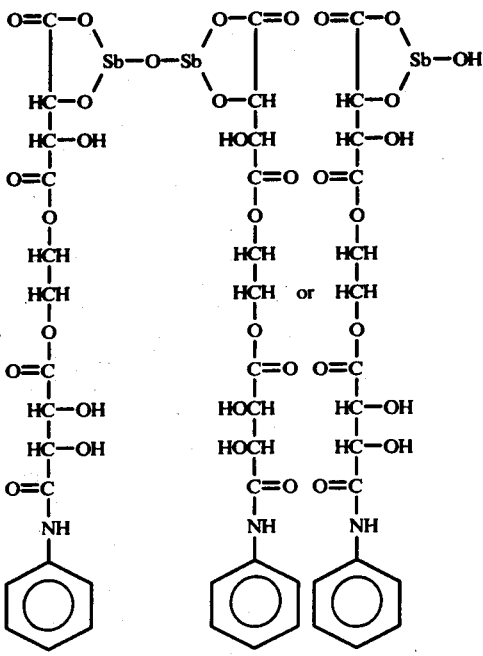

are only present in small quantities in the reaction mixture.

By virtue of their substantial insolubility in water, their high solubility in organic solvents and their excellent compatibility with acrylonitrile-vinyl or vinylidene halide copolymers, the new reaction products are suitable for addition to the above-mentioned polymers as extremely effective corrosion-free flameproofing agents which cannot be washed out with water.

In the following Examples, which are to further illustrate the invention without limiting it, all percentages are by weight.

EXAMPLE 1

(Solution A)

480 parts by weight of tartaric acid and 99.2 parts by weight of ethylene glycol in the presence of 3.2 parts by weight of an acid ion exchanger (Lewatit S 100, a product of Bayer AG) are condensed with stirring for 5 hours at 140° C in a condensation apparatus, while nitrogen is passed over, until the stoichiometric quantity of 57.6 parts by weight of water has distilled off. The esterification product is then dissolved in 768 parts by weight of dimethyl formamide. Following the addition of about 20 parts by weight of active carbon, the solution is filtered off from the ion exchanger and the active carbon. 116.6 parts by weight of antimony trioxide are added to the solution obtained, followed by heating with stirring at 150° C, while nitrogen is passed over, until after about 40 minutes a clear solution is obtained and the stoichiometric quantity of water has distilled off. The solution is then cooled at 20° C and phenyl isocyanate is added dropwise at a temperature in the range of from 20° to 40° C until no more carbon dioxide is given off. The consumption of phenyl isocyanate amounts to 182 parts by weight. The solution is then stirred for about 2 hours at 40° C.

The solution obtained is readily miscible and compatible with solutions of copolymers of acrylonitrile and vinyl or vinylidene chloride. The complex antimony compound precipitates on the addition of water to the dimethyl formamide solution.

EXAMPLE 2

(Solution B)

In a condensation apparatus, 300 parts by weight of tartaric acid together with 118 parts by weight of 1,6-hexane diol and 3 parts by weight of an acid ion exchanger (Lewatit S 100, a product of Bayer AG) are heated with stirring for about 10 hours at 140° C, wile nitrogen is passed over, until the stoichiometric quantity of water (36 parts by weight) has distilled off. The reaction product is dissolved in 516 parts by weight of dimethyl acetamide and the solution is freed from the acid catalyst by filtration. 102.9 parts by weight of antimony trioxide are then added and the dispersion is heated with stirring for approximately 50 minutes at 150° C, while nitrogen is passed over, until a clear solution is obtained. After cooling to approximately 25° C, a solution of 34.2 parts by weight of methyl isocyanate in 100 parts by weight of dimethyl acetamide is added dropwise in such a way that the temperature does not exceed 40° C. The solution is then stirred for 2 hours at 40° C. A slight deposit may form from the almost colourless solution in the event of prolonged standing, although it is completely dissolved on admixture with a solution of an acrylonitrile-vinyl chloride copolymer is dimethyl acetamide. The complex antimony compound precipitates on the addition of water to its solution.

EXAMPLE 3

(Solution C)

Following the procedure of Example 2, 210 parts by weight of citric acid and 62 parts by weight of ethylene glycol in the presence of 2 parts by weight of an acid ion exchanger (Lewatit S 100, a product of Bayer AG) are condensed under nitrogen for 6 hours at 140° C. The condensation product is then dissolved in 285 parts by weight of dimethyl formamide and filtered while still warm. Following the addition of 43.7 parts by weight of antimony trioxide, the mixture is heated for approximately 40 minutes at 150° C until a clear solution is obtained. The solution is then cooled to room temperature, followed by the addition in portions of 75.2 parts by weight of 3,4-dichlorophenyl isocyanate. The temperature should not exceed 40° C. The solution is then stirred for 2 hours at 40° C.

The complex antimony compound is insoluble in water, whilst its solution is compatible with solutions of copolymers of acrylonitrile and vinyl or vinylidene halides.

EXAMPLE 4

(Solution D)

In an apparatus of the kind described in Example 1, 1012 parts by weight of glycerol and 4950 parts by weight of tartaric acid in the presence of 33 parts by weight of an acid ion exchanger (Lewatit S 100, a product of Bayer AG) are condensed with stirring under a nitrogen atmosphere for about 6 hours at a bath temperature of 170° C until no more water distils off. The product of condensation is then dissolved in 18,565 parts by weight of dimethyl formamide and filtered following the addition of 500 parts by weight of active carbon. 1202 parts by weight of antimony trioxide are added to the filtered solution, followed by heating at 140° to 150° C, while nitrogen is passed over, until a clear, pale yellowish solution has formed from the dispersion. After cooling to room temperature, 4653 parts by weight of 3,4-dichlorophenyl isocyanate are added in portions with evolution of carbon dioxide in such a way that the temperature does not exceed 50° to 60° C.

The antimony compound precipitates on the addition of water.

A solution of the complex antimony compound in dimethyl formamide is compatible in any mixing ratios with dimethyl formamide solutions of copolymers of acrylonitrile and vinyl or vinylidene chloride.

EXAMPLE 5

The complex antimony solutions A, B, C and D described in Examples 1 to 4 are added in various quantities to a 35% dimethyl formamide solution of an acrylonitrile-vinylidene chloride copolymer of 58.6% of acrylonitrile, 38.5% of vinylidene chloride and 2.9% of sodium methallyl sulphonate with a K-value according to Fikentscher (Cellulosechemie 13 (1932), page 58) of 75.3. The resulting polymer solutions with the antimony additives are spun into filaments by conventional dry-spinning processes, stretched in hot water and washed in the usual way.

The results of the vertical burning test according to DIM 53 906 carried out on pieces of knitting produced from the resulting fibre yarns are set out in the following Table:

| Solution added | Antimony content [%] Original | Antimony content [%] Found in the piece of the knitting | Ignition time [secs.] | Burning time* [secs.] | Distance burnt [cm] max: 35 cm |
|---|---|---|---|---|---|
| Comparison test without any addition | | | 3 | 48 | 32.5 |
| | | | 3 | 29 | 32.5 |
| | | | 3 | 27 | 20.0 |
| | | | 15 | 25 | 32.5 |
| | | | 15 | 27 | 32.5 |
| | | | 15 | 26 | 32.5 |
| A | 0.5 | 0.5 | 3 | 16 | 15.0 |
| | | | 3 | 16 | 13.0 |
| | | | 3 | 19 | 14.5 |
| | | | 15 | 12 | 9.5 |
| | | | 15 | 15 | 11.0 |
| | | | 15 | 17 | 11.5 |
| | | | 3 | — | 1.0 |
| | | | 3 | — | 1.0 |
| A | 2.0 | 1.9 | 3 | 1 | 1.5 |
| | | | 15 | — | 1.5 |
| | | | 15 | 1 | 2.0 |
| | | | 15 | — | 1.0 |
| | | | 3 | — | 1.0 |
| | | | 3 | — | 1.5 |
| B | 2.5 | 2.5 | 3 | — | 1.0 |
| | | | 15 | — | 1.5 |
| | | | 15 | — | 1.5 |
| | | | 15 | — | 1.0 |
| | | | 3 | — | 1.5 |
| | | | 3 | 1 | 3.5 |
| B | 1.5 | 1.4 | 3 | — | 2.0 |
| | | | 15 | 1 | 3.0 |
| | | | 15 | — | 1.5 |
| | | | 15 | 1 | 2.0 |
| | | | 3 | 1 | 2.5 |
| | | | 3 | — | 1.5 |
| C | 1.8 | 1.6 | 3 | — | 1.0 |
| | | | 15 | — | 1.0 |
| | | | 15 | 1 | 1.5 |
| | | | 15 | 1 | 1.5 |
| | | | 3 | — | 1.0 |
| | | | 3 | — | 1.0 |
| D | 1.7 | 1.7 | 3 | — | 1.0 |
| | | | 15 | 1 | 2.0 |
| | | | 15 | — | 1.0 |
| | | | 15 | 2 | 1.5 |

*following removal of the ignition flame

What we claim is:

1. A process for the production of a solution of a substantially water-insoluble complex antimony compound in a polar organic solvent which comprises esterifying an α-hydroxy polycarboxylic acid with a polyol in a molar ratio of the carboxyl groups to the hydroxyl groups in the polyol of at least 2 : 1 and in the presence of an acid transesterification catalyst; reacting an excess of the esterification product with an antimony oxide in a polar organic solvent at a temperature in the range of from 100° to 200° C to form a clear solution still containing free carboxyl groups; and adding a monoisocyanate to the solution at a temperature below 100° C in such a quantity that the free carboxyl groups are converted into the corresponding amide groups the monoisocyanate corresponding to the general formula

$R_1-N=C=O$ in which $R_1$ is a straight-chain or branched alkyl group having from 1 to 20 carbon atoms, or

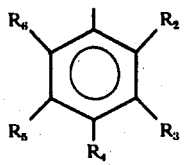

in which $R_2$, $R_3$, $R_4$, $R_5$ and $R_6$ may be the same as or different from one another and may represent a member selected from the group consisting of hydrogen, an alkyl having from 1 to 5 carbon atoms, fluorine, chlorine or bromine.

2. The process of claim 1, wherein said polar organic solvent is a member selected from the group consisting of dimethyl formamide, dimethyl acetamide, N-methyl pyrrolidone and dimethyl sulphoxide.

3. The process of claim 1, wherein said antimony oxide is antimony trioxide.

4. The process of claim 1, wherein said α-hydroxy polycarboxylic acid is tartaric acid or citric acid.

5. The process of claim 1, wherein said polyol is a compound corresponding to the formula $R(OH)_n$, in which R is a straight-chain or branched aliphatic group having from 2 to 20 carbon atoms and $n$ is a number from 2 to 6.

6. The process of claim 1, wherein said esterification of said α-hydroxy polycarboxylic acid with said polyol is carried out at a temperature in the range of from 100° to 180° C.

7. The process of claim 1, wherein the molar excess of the carboxyl groups in the esterification product relative to the antimony amounts to between 2 : 1 and 4 : 1.

8. A solution of a complex antimony compound in a polar organis solvent when produced according to claim 1.

* * * * *

UNITED STATES PATENT AND TRADEMARK OFFICE
CERTIFICATE OF CORRECTION

PATENT NO. : 4,018,809
DATED : April 19, 1977
INVENTOR(S) : Eduard Radlmann et al It is certified that error appears in the above—identified patent and that said Letters Patent are hereby corrected as shown below:

On the cover sheet Assignee should read:
-----BAYER AKTIENGESELLSCHAFT, Leverkusen, Germany-----

On the cover sheet Attorney, Agent or Firm has been omitted and should be put in ---PLUMLEY AND TYNER---

Col. 1, line 12, U.S. Pat. No. should be ---US-PS---

Col. 4, line 19, (Lewatit S100 should be ---(Lewatit$^{(R)}$ S100---

Col. 4, line 50 (Lewatit S 100 should be--- (Lewatit$^{(R)}$ S 100---

Col. 4, line 51, 'wile should be ---while---

Col. 5, line 1, is should be ---in---

Col. 5, line 10 (Lewatit S 100 should be ---Lewatit$^{(R)}$ S 100---

Claim 8, organis should be ---organic---

Signed and Sealed this

Eighteenth Day of October 1977

[SEAL]

Attest:

RUTH C. MASON
*Attesting Officer*

LUTRELLE F. PARKER
*Acting Commissioner of Patents and Trademark*